(12) United States Patent
Bonnet

(10) Patent No.: US 9,265,448 B2
(45) Date of Patent: Feb. 23, 2016

(54) SYSTEM AND METHOD FOR DETECTING THE WALK OF A PERSON

(75) Inventor: Stéphane Bonnet, Lyons (FR)

(73) Assignees: COMMISSARIAT A L'ENERGIE ATOMIQUE ET AUX ENERGIES ALTERNATIVES, Paris (FR); MOVEA, Grenoble (FR)

(*) Notice: Subject to any disclaimer, the term of this patent is extended or adjusted under 35 U.S.C. 154(b) by 1112 days.

(21) Appl. No.: 13/203,461

(22) PCT Filed: Feb. 25, 2010

(86) PCT No.: PCT/EP2010/052368
§ 371 (c)(1),
(2), (4) Date: Oct. 31, 2011

(87) PCT Pub. No.: WO2010/097422
PCT Pub. Date: Sep. 2, 2010

(65) Prior Publication Data
US 2012/0041713 A1 Feb. 16, 2012

(30) Foreign Application Priority Data
Feb. 26, 2009 (FR) .................................... 09 51212

(51) Int. Cl.
*G01C 22/00* (2006.01)
*A61B 5/103* (2006.01)
(Continued)

(52) U.S. Cl.
CPC ............. *A61B 5/1038* (2013.01); *A61B 5/1118* (2013.01); *A61B 5/1123* (2013.01); *G01C 21/165* (2013.01); *G01C 22/006* (2013.01); *G06F 17/16* (2013.01)

(58) Field of Classification Search
CPC .... G01C 22/006; G01C 21/165; G01B 21/02; G06F 17/16
USPC .......................................... 702/160, 155, 158
See application file for complete search history.

(56) References Cited

U.S. PATENT DOCUMENTS

| | | | | |
|---|---|---|---|---|
| 6,011,990 A | * | 1/2000 | Schultz et al. | 600/544 |
| 2003/0153847 A1 | * | 8/2003 | Sandler et al. | 600/587 |

(Continued)

FOREIGN PATENT DOCUMENTS

| | | | |
|---|---|---|---|
| JP | 2007-160076 | * | 6/2007 |
| JP | 2007 160076 A | | 6/2007 |

OTHER PUBLICATIONS

Kavanagh J J et al.: "Coordination of head and trunk accelerations during walking", European Journal of Applied Physiology, Jul. 1, 2005, pp. 468-475.

(Continued)

*Primary Examiner* — An Do
(74) *Attorney, Agent, or Firm* — Stroock & Stroock & Lavan LLP

(57) ABSTRACT

A system for detecting the walk of a person has a housing (BT) with at least a biaxial movement sensor (CM). The housing is attached to the upper portion of the body of the person, so that a first measurement axis of the sensor (CM) coincides with the anteroposterior axis (AP) or the vertical axis (VT) of the body and so a second measurement axis of said sensor (CM) coincides with the mediolateral axis (ML) of the body. An analysis means (MA) analyzes the measurements delivered by the sensor (CM). The analysis means includes a processing means (MT) for processing over a time window the measurement signals delivered by the sensor (CM), which includes means for searching for a dominant frequency (MRFD) in said signals. The analysis means also includes a detection means (MD) for detecting the walk of the person when a ratio between the dominant frequency of the signal of the first measurement axis and the dominant frequency of the second measurement axis, or between the dominant frequency of a Euclidian norm of the vector of measurements transmitted by the sensor (CM) and the dominant frequency of the signal of the second measurement axis, is substantially equal to two.

16 Claims, 5 Drawing Sheets

(51) Int. Cl.
*G01C 21/16* (2006.01)
*G06F 17/16* (2006.01)
*A61B 5/11* (2006.01)

(56) References Cited

U.S. PATENT DOCUMENTS

| | | | |
|---|---|---|---|
| 2004/0064438 A1* | 4/2004 | Kostoff | 707/1 |
| 2004/0073098 A1* | 4/2004 | Geva et al. | 600/300 |
| 2004/0116837 A1* | 6/2004 | Yamaguchi et al. | 600/595 |
| 2005/0205656 A1* | 9/2005 | Sugai | 235/105 |
| 2006/0122526 A1* | 6/2006 | Berenfeld et al. | 600/515 |
| 2006/0148619 A1* | 7/2006 | Tsubata et al. | 482/8 |
| 2006/0279426 A1* | 12/2006 | Bonnet et al. | 340/573.1 |
| 2008/0004834 A1* | 1/2008 | Sugai | 702/160 |
| 2008/0004904 A1* | 1/2008 | Tran | 705/2 |
| 2008/0027675 A1* | 1/2008 | Noguchi et al. | 702/160 |
| 2008/0077353 A1* | 3/2008 | Tsubata | 702/160 |
| 2008/0190202 A1* | 8/2008 | Kulach et al. | 73/514.01 |
| 2008/0294019 A1* | 11/2008 | Tran | 600/301 |
| 2009/0137918 A1* | 5/2009 | Noffsinger et al. | 600/529 |
| 2009/0177037 A1* | 7/2009 | Viswanathan et al. | 600/118 |
| 2009/0181636 A1* | 7/2009 | Fulks et al. | 455/334 |
| 2009/0192708 A1* | 7/2009 | Yoo et al. | 701/213 |
| 2010/0234775 A1* | 9/2010 | Yasuhara et al. | 601/33 |

OTHER PUBLICATIONS

International Search Report and Written Opinion dated May 4, 2010, issued in counterpart International Application No. PCT/EP2010/052368.

* cited by examiner

SYSTEM AND METHOD FOR DETECTING THE WALK OF A PERSON

CROSS-REFERENCE TO RELATED APPLICATIONS

This application is a national phase application under §371 of PCT/EP2010/052368, filed Feb. 25, 2010, which claims priority to French Patent Application No. 0951212, filed Feb. 26, 2009, both of which are incorporated herein in their entirety.

FIELD OF THE INVENTION

Embodiments of the invention relate to a system and a method for detecting the walk of a person, or, in other words, for detecting a movement of a person by a mode of locomotion consisting of a sequence of steps.

BACKGROUND

Systems for the analysis of movement of persons are becoming increasingly widespread in the biomedical field, notably for analyzing the physical activity of a person.

The detection of the walking activity of a person provides information which makes it possible, for example, to estimate an energy expenditure of a person, to evaluate a level of sedentariness of a person, or to estimate the quality or loss of functional capacity after a surgical intervention or a medicinal treatment.

A document entitled "Ambulatory system for human motion analysis using a kinematic sensor: monitoring of daily physical activity in the elderly," *Biomedical Engineering, IEEE Transactions on*, vol. 50, no. 6, pp. 711-723, June 2003, by Najafi, B., Aminian, K., Paraschiv-Ionescu A., Loew, F., Bula C. J., and Robert, P., describes a 2A1G movement sensor (a biaxial accelerometer and monoaxial gyrometer that is worn on the trunk of a person and of which the vertical acceleration signal is filtered by a 0.62-5.00 Hz band-pass filter). At least three evenly-spaced occurrences of peak amplitude higher than a threshold are sought on this filtered signal. It is difficult to set a universal threshold a priori, which notably involves a lack of reliability of such a system.

A document entitled "Reference data for normal subjects obtained with an accelerometric device", Gait & Posture, October 2002 Vol. 16, Issue 2, Pages 124-134, by Bernard Auvinet, Gilles Berrut, Claude Touzard, Laurent Moutel, Nadine Collet, Denis Chaleil, and Eric Barrey, describes a frequential analysis of a walking activity considered to be a substantially periodic activity, which creates a power peak at a frequency that depends on the walking speed. The study of the ratio between even and odd harmonics of the vertical acceleration signal makes it possible to study the stability of the walk. This does not involve detecting a walking activity, but analyzing or characterizing a walking activity of a person when it is already known that the person is walking.

The document entitled "Classification of waist-acceleration signals in a continuous walking record", Medical Engineering & Physics 22 (4) (2000), pp. 285-291, by M. Sekine, T. Tamura, T. Togawa and Y. Fukui, describes the use of a wavelet transform to distinguish, in a signal representative of the walk of a person, whether the latter is walking on a horizontal surface, climbing stairs or going down stairs. The content of this document does not make it possible to detect a walking activity.

SUMMARY OF THE INVENTION

An object of embodiments of the present invention is to detect walking activities of a person in a record of ambulatory signals of this person.

According to one aspect of the invention, a system is proposed for detecting the walk of a person, furnished with a housing comprising a biaxial or triaxial movement sensor. The housing is suitable for being attached to the upper portion of the body of said person, so that a first measurement axis of said sensor is adapted to provide measurements representative of the anteroposterior axis or the vertical axis of said body and so that a second measurement axis of said sensor is adapted to provide measurements representative of the mediolateral axis of said body, said system also being furnished with analysis means for analyzing the measurements delivered by said sensor. Said analysis means comprises:
   processing means for processing over a time window the measurement signals delivered by said sensor, comprising means for searching for a dominant frequency in said signals, and
   detection means for detecting the walk of the person when a ratio between the dominant frequency of the signal of the first measurement axis and the dominant frequency of the second measurement axis, or between the dominant frequency of a Euclidian norm of the vector of measurements transmitted by said sensor and the dominant frequency of the signal of the second measurement axis, is substantially equal to two.

Such a system makes it possible, at reduced cost and with little discomfort for the person wearing it, to detect the walk of a person, in a robust and automatic manner.

For example, the time window can be a sliding window.

Therefore the system is extremely precise even over a considerable processing period.

In one embodiment, said movement sensor is triaxial, the first measurement axis of said sensor coincides with the anteroposterior axis of said body, the second measurement axis of said sensor coincides with the mediolateral axis of said body, and the third measurement axis of said sensor coincides with the vertical axis of said body. Said detection means are suitable for detecting a ratio substantially equal to two between the dominant frequency of the signal of the first measurement axis and the dominant frequency of the second measurement axis, or between the dominant frequency of the signal of the third measurement axis and the dominant frequency of the second measurement axis, or between the dominant frequency of a Euclidian norm of the vector of measurements transmitted by said sensor and the dominant frequency of the signal of the second measurement axis.

Therefore, the precision of detection is improved.

According to one embodiment, the system also comprises high-pass filters.

The respective continuous components of the signals transmitted by the movement sensor are therefore removed in order to be able to detect the dominant frequency with great precision.

In one embodiment, the system also comprises pass-band filters, for example with a frequency band of between 0.5 and 10 Hz.

The influence of signal noise or frequencies having no relationship with the walk is therefore greatly restricted.

According to one embodiment, said analysis means are internal or external to said housing, and said movement sensor comprises wired or wireless transmission means for transmitting its measurements to said analysis means.

The analysis means may be incorporated into the housing or installed on a remote base and the output signals from the housing, whether or not analyzed, can be transmitted with or without wire.

Said movement sensor may be a biaxial or triaxial accelerometer, a biaxial or triaxial magnetometer, or a biaxial or triaxial gyrometer.

Embodiments of the invention work with all these types of movement sensors.

For example, the sliding time window can last for five seconds, with a partial overlap of four seconds between two consecutive windows offset by one second.

These values are particularly well-suited to the walk of a person.

According to one embodiment, said means for searching for a dominant frequency for the signals transmitted by the movement sensor are suitable for carrying out the search for dominant frequency, in each time window, by spectral analysis. For example, this spectral analysis can be of the spectrogram type.

The spectrogram, which uses the square of the modulus of the Fourier transform of the signal convoluted with an apodization window, is a simple, reliable and low-cost method of searching for a dominant frequency, that is to say the frequency corresponding to the maximum signal power.

Said means for searching for a dominant frequency may be suitable for limiting the search for a dominant frequency $\square_{ML}$ along the second axis at frequencies of between 0.25 Hz and 1 Hz.

Said means for searching for a dominant frequency may be suitable for limiting the search for a dominant frequency along the first axis, when the latter coincides with the anteroposterior axis, at frequencies in a predetermined frequency range. This frequency range can be bounded by the dominant frequency along the second axis $f_{ML}$ Hz increased by 0.2 Hz and 3 Hz ($[f_{ML}+0.2; 3]$).

Preferably, this range may be bounded by the dominant frequency along the second axis $f_{ML}$ Hz increased by 0.25 Hz and 2 Hz, ($[f_{ML}+0.25; 2]$).

Said means for searching for a dominant frequency may be suitable for limiting the search for a dominant frequency along the first axis, when the latter coincides with the vertical axis, at frequencies included in a predetermined frequency range. This frequency range may be bounded by the dominant frequency along the second axis $f_{ML}$ Hz increased by 0.2 Hz and 3 Hz ($[f_{ML}+0.2; 3]$).

Said means for searching for a dominant frequency may be suitable for limiting the search for a dominant frequency, for the Euclidian norm of the vector of measurements transmitted by said movement sensor, at frequencies included in a predetermined frequency range. This frequency range may be bounded by the dominant frequency along the second axis $f_{ML}$ Hz increased by 0.2 Hz and 3 Hz ($[f_{ML}+0.2; 3]$).

All of these values are particularly well-suited to walking activities.

According to one embodiment, said detection means are suitable for detecting a ratio of said dominant frequencies substantially equal to two, to within a variance, when, at least on one axis, the signal power, at at least one frequency, is also higher than a threshold.

In other words, such a ratio is determined, or used, only for the windows that have, on at least one axis, at least one frequency, the power of which is higher than a determined threshold, this threshold being able to be called the power threshold. This power threshold is determined a priori, or adjusted experimentally, for example during a test phase.

It is possible to apply this condition of power of at least one frequency to at least one axis, but also to all the axes. It is noted that, when this power condition is applied to various axes, each power threshold may be different from another.

According to a particular embodiment, said determination means are suitable for determining the ratio of the dominant frequencies, corresponding to a given time window, when, on at least one axis, the dominant frequency has a power higher than a threshold power.

It is possible to apply this threshold condition only to the dominant frequency, or equally to other defined frequencies or frequency bands.

It is noted that this power threshold criterion may also be applied to the Euclidian norm of the measurement vector. For each time window, the frequency or frequencies, for example the dominant frequency, will then be verified, having a power higher than a power threshold.

This power threshold may be set a priori or by determining in advance a power in a time slot during which nothing happens, for example during the anatomical calibration.

According to one embodiment, said housing is suitable for being attached to the torso or to the sacrum of said person.

When the housing is attached to the torso, the amplitude of the oscillations of the trunk is higher, which improves the precision of the system.

The attachment to the sacrum is particularly easy and discreet, for example by means of a belt.

According to another aspect of the invention, a method for detecting the walk of a person is provided, based on measurements taken by a biaxial or triaxial movement sensor, in which movements along a first measurement axis of said sensor are adapted to provide measurements representative of the anteroposterior axis or the vertical axis of the body of said person and along a second measurement axis of said sensor are adapted to provide measurements representative of the mediolateral axis of said body, in which:

over a time window, the measurement signals delivered by said movement sensor are processed, said processing comprising a search for a dominant frequency in said signals, and the walk of said person is detected when a ratio between the dominant frequency of the signal of the first measurement axis and the dominant frequency of the second measurement axis, or between the dominant frequency of a Euclidian norm of the vector of measurements transmitted by said sensor and the dominant frequency of the signal of the second measurement axis, is substantially equal to two.

For example, the processing can be carried out over a sliding time window.

BRIEF DESCRIPTION OF THE DRAWINGS

The invention will be better understood on studying a number of embodiments described as nonlimiting examples and illustrated by the appended drawings in which.

DETAILED DESCRIPTION OF THE PREFERRED EMBODIMENT

In all of the figures, the elements that have the same references are similar.

Figure 1:
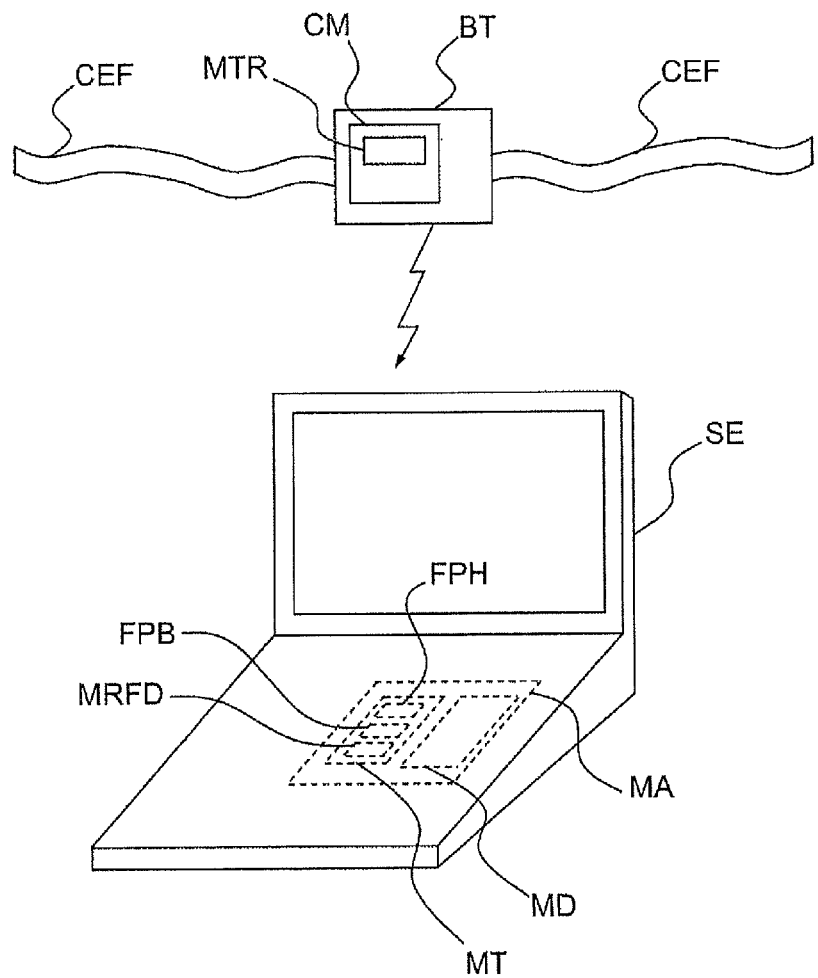
FIG. 1 illustrates schematically one embodiment of a system according to one aspect of the invention.

As illustrated in FIG. 1, a system for detecting the walk of a person comprises a housing BT comprising a biaxial or triaxial movement sensor CM. The housing BT is suitable for being attached to the upper portion of the body of said person, in this instance by means of an elastic attachment belt CEF, so that a first measurement axis of said movement sensor is adapted to provide measurements representative of the anteroposterior axis AP or the vertical axis VT of said body and that a second measurement axis of said movement sensor is adapted to provide measurements representative of the mediolateral axis ML of said body. As a variant, any other means of attachment may be appropriate.

For example, the first measurement axis of the motion sensor may coincide with the anterior-posterior axis AP or with the vertical axis VT of the body, and the second measurement axis of the motion sensor may coincide with mediolateral axis ML of the body.

This coincidence may, for example, be achieved by anatomical calibration, for example by asking the person to whom the housing BT has been attached to stand as straight as possible for a few seconds against a wall. The system, in a known manner, determines the rotation matrix to be applied to the measurements in order to deliver measurements reduced to the mediolateral axis ML, anteroposterior axis AP or vertical axis VT. The movement sensor CM is also provided with a transmission module MTR in order to transmit the measurements, in this example by wireless transmission, to an external station SE, in this case a laptop computer.

As a variant, the transmission could be by wire. The movement sensor may, for example, be a biaxial or triaxial accelerometer, a biaxial or triaxial magnetometer, or a biaxial or triaxial gyrometer.

However, in the rest of the description, in a nonlimiting manner, the movement sensor CM will be a biaxial accelerometer the first measurement axis of which coincides with the anteroposterior axis AP of the body of the person and the second measurement axis coincides with the mediolateral axis ML of the body of the person.

As a variant, the second measurement axis of the accelerometer may coincide with the mediolateral axis ML of the body of the person and the first measurement axis may coincide with the vertical axis VT of the body of the person.

The laptop computer SE comprises an analysis module MA for analyzing the data transmitted by the accelerometer CM. As a variant, the analysis module may be incorporated into the housing BT.

The analysis module is suitable for sampling the signals received from the accelerometer CM at a sampling frequency that is below or equal to 1 kHz, and typically of the order of 10 to 200 Hz.

The analysis module MA comprises a processing module MT for processing the measurement signals delivered by the accelerometer CM.

As a variant, in the case of a triaxial movement sensor CM, such as a triaxial accelerometer, it is possible to carry out an anatomical calibration so that the first measurement axis of the accelerometer coincides with the anteroposterior axis AP of the body of the person, the second measurement axis of the accelerometer coincides with the mediolateral axis ML of the body of the person, and the third measurement axis of the accelerometer coincides with the vertical axis VT of the body of the person. In this case, the detection module is suitable for detecting a ratio substantially equal to two, between the dominant frequency of the signal of the first measurement axis and the dominant frequency of the second measurement axis, or between the dominant frequency of the signal of the third measurement axis and the dominant frequency of the second measurement axis, or between the dominant frequency of a Euclidian norm of the vector of measurements transmitted by said sensor and the dominant frequency of the signal of the second measurement axis. This then gives improved precision of detection.

A ratio that is substantially equal to 2 means a ratio for example of between 1.7 and 2.3, and preferably between 1.9 and 2.1.

This ratio may be predetermined, but equally adjusted experimentally, notably during a test phase. The various values taken by this ratio are then analyzed precisely when the person is walking, and the critical value that will then be used in the algorithm is determined. This determination may notably be made statistically, considering the risks associated with false positives (the device signals that the person is walking while he is not walking) or with false negatives (the device indicates that the person is not walking when he is walking).

The processing module MT may comprise high-pass filters FPH making it possible to remove the respective continuous components of the signals transmitted by the accelerometer CM in order to detect the dominant frequency with great precision.

The processing module MT may also comprise band-pass filters so as to greatly limit the influence of signal noise or frequencies that have no relation to the walking.

Moreover, the processing module MT comprises a module for searching for a dominant frequency MRFD for the signals transmitted by the movement sensor, by spectral analysis. The spectral analysis, which can include estimating the power of the signal as a function of the frequency, is a known method that is simple and low-cost in terms of computations for searching for a dominant frequency in a signal. A "dominant frequency" is understood to be the frequency that corresponds to the maximum of the power density of the signal. Naturally, as a variant, any other method of searching for a dominant frequency MRFD may be envisaged. For example, the spectral analysis may be carried out by using a Fourier transform, but also other techniques known to those skilled in the art, for example a wavelet transform, a technique that is better suited to nonstationary signals.

The analysis module MA also comprises a detection module MD for detecting the walk of the person when a ratio between the dominant frequency of the signal of the first measurement axis and the dominant frequency of the second measurement axis, or between the dominant frequency of a Euclidian norm of the vector of measurements transmitted by said sensor and the dominant frequency of the signal of the second measurement axis, is substantially equal to two.

Embodiments of the present invention work without requiring physical calibration of the movement sensor CM, or, in other words, a system according to embodiments of the invention works based on the raw data expressed in numerical units or in volts and knowledge of the gains and shifts of the movement sensor CM is not essential. If it is decided not to convert the volts into physical units (for example m/s² for an accelerometer) the concept of minimal power threshold may be decided upon based on a measurement of the person in a state of rest and not based on kinematic data.

Figure 2:
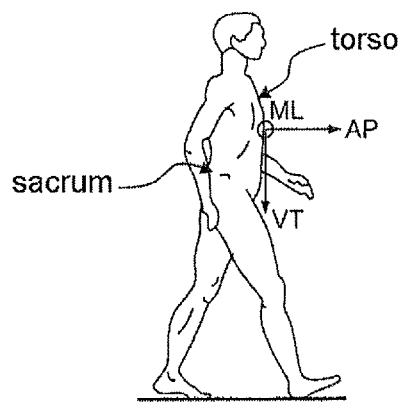
FIG. 2 represents schematically a person and his anteroposterior, vertical and mediolateral anatomical axes.

FIG. 2 illustrates schematically a person, and his three anatomical axes, the mediolateral axis ML, the anteroposterior axis AP, and the vertical axis VT, oriented so that the trihedron (ML, VT, AP) is a direct trihedron. The mediolateral axis ML of the body is oriented from the left portion of the body to the right portion of the body, the anteroposterior axis AP is oriented from the rear portion of the body to the front portion of the body and the vertical axis is oriented from the upper portion of the body to the lower portion of the body.

Optimally, the housing may be placed on the torso, or on the sacrum.

The band-pass filter FPB may, for example, be a 4th order Butterworth filter filtering in the frequency band between 0.5 and 10 Hz, particularly well suited to walking.

The signals are divided into time windows for analysis, the time windows preferably being sliding time windows, for example into windows of five seconds, with a partial overlap of four seconds between two consecutive windows offset by one second. For each time window, dominant frequencies of signals are then sought.

The module for searching for a dominant frequency MRFD by spectral analysis of the spectrogram type may be adapted to limit the search for a dominant frequency along the first axis $f_{ML}$ at frequencies of between 0.25 Hz and 1 Hz.

The module for searching for a dominant frequency MRFD by spectral analysis may also be adapted to limit the search for a dominant frequency along the first axis, when the latter coincides with the anteroposterior axis AP, at frequencies between the dominant frequency along the second axis $f_{ML}$ Hz increased by 0.2 Hz and 3 Hz, or at frequencies between the dominant frequency along the second axis $f_{ML}$ Hz increased by 0.25 Hz and 2 Hz ($[f_{ML}+0.25; 2]$).

The module for searching for a dominant frequency MRFD by spectral analysis may also be adapted to limit the search for a dominant frequency along the first axis, when the latter coincides with the vertical axis VT, at frequencies between the dominant frequency along the second axis $f_{ML}$, Hz increased by 0.2 Hz and 3 Hz.

The module for searching for a dominant frequency MRFD by spectral analysis may also be adapted to limit the search for a dominant frequency for the Euclidian norm of the vector of measurements transmitted by said movement sensor CM, at frequencies between the dominant frequency along the second axis $f_{ML}$ Hz increased by 0.2 Hz and 3 Hz.

All these limitations of the searches for the dominant frequency are particularly suitable for walking, and make it possible to limit the computation time and the memory size used.

Moreover, tests have shown that the choice of such frequency ranges, in which the search for a dominant frequency is restricted, made it possible to increase reliability, and even stability, by notably reducing the risks of false positives or false negatives.

Figure 3:
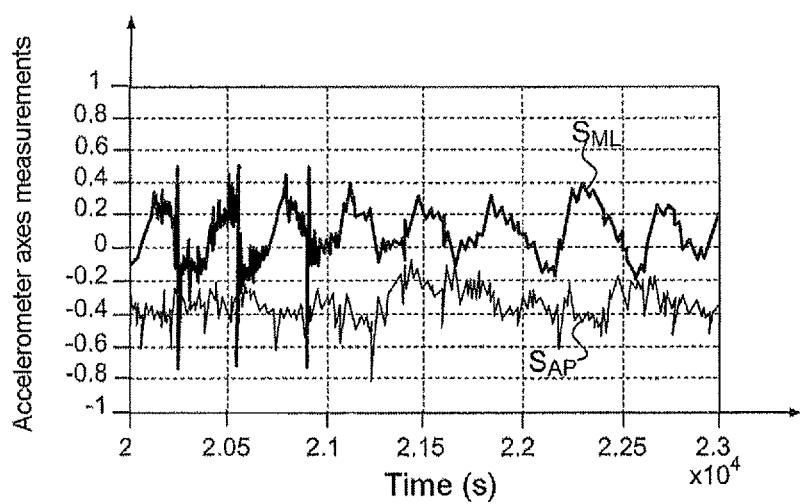
FIG. 3 illustrates an example of measurements taken by a system according to FIG. 1, in which the movement sensor is a biaxial accelerometer.

FIG. 3 shows an example of signals $S_{ML}$ and $S_{AP}$ transmitted by a housing BT according to one aspect of the invention, furnished with a biaxial accelerometer CM, the first measurement axis of which coincides with the anteroposterior axis AP and the second measurement axis of which coincides with the mediolateral axis ML, as a function of time. The housing BT is, for example, placed on the sacrum of the person whose activity is being monitored.

Figure 4:
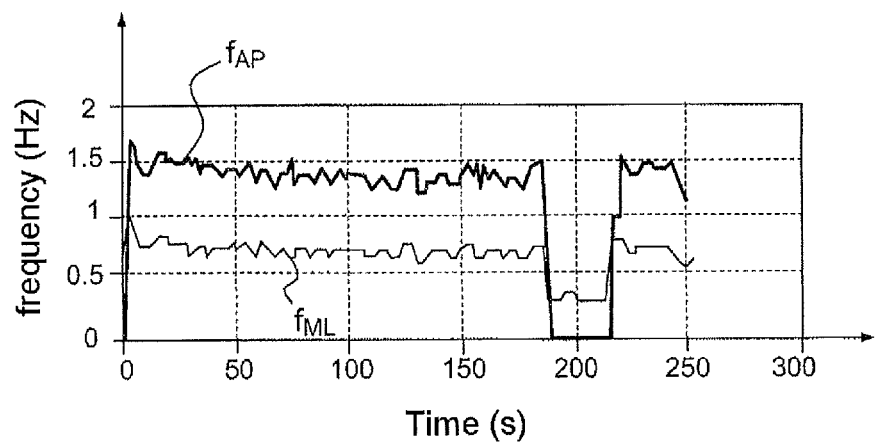
FIGS. 4 and 5 illustrate the operation of the analysis means.

FIG. 4 represents, for the case of the data of FIG. 3, the dominant frequencies $f_{ML}$ and $f_{AP}$ as a function of time, corresponding to the signals $S_{ML}$ and $S_{AP}$, the dominant frequencies $f_{ML}$ and $f_{AP}$ being computed by the module for searching for a dominant frequency MRFD, by a sliding window.

Figure 5:
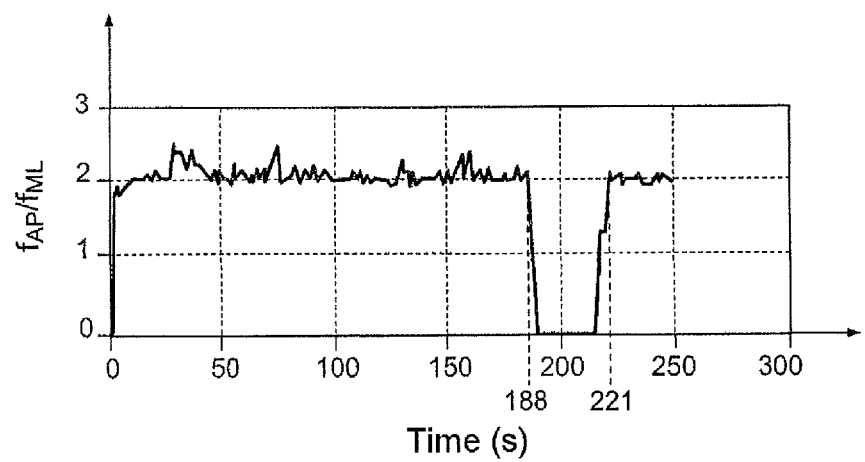

FIG. 5 represents, for the case of FIGS. 3 and 4, the computation, by the walking detection module MD based on the ratio of the dominant frequencies $f_{ML}$ and $f_{AP}$. The system then detects a walking activity between the moments corresponding to the initial moment 0 s and the moment corresponding to 182 s after the initial moment, and a walking activity resuming after the moment corresponding to 221 s after the initial moment.

In the following exemplary embodiments, in which a user wears a walking detection system according to one aspect of the invention, with which he adopts various postures, immobile or moving, during various tests.

The measurements are taken, in this instance, at a sampling rate of 200 Hz. These data are grouped together over a sliding window lasting 10 s, with an overlap of 90% between two consecutive windows. A band-pass filtering [0.1 Hz; 10 Hz] is applied to these measurements by a 4th order IIR Butterworth filter. A spectral analysis of each window is carried out by computing the square of the Fourier transform modulus of the product of the signal measured multiplied by the apodization window, making it possible to arrive at a spectrogram. The dominant frequency $f_{ML}$ on the second axis is determined on each window.

In these examples, for each measurement axis, the dominant frequency is determined in a respective preferred range of frequency values: $f_{ML}$ between 0.25 Hz and 1 Hz, and $f_{AP}$ between $f_{ML}+0.25$ and 2 Hz.

Figure 6A:
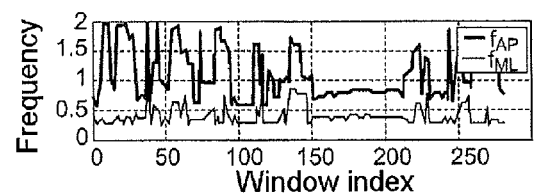
FIGS. 6a and 6b illustrate a first embodiment of the system according to one aspect of the invention.
Figure 6B:
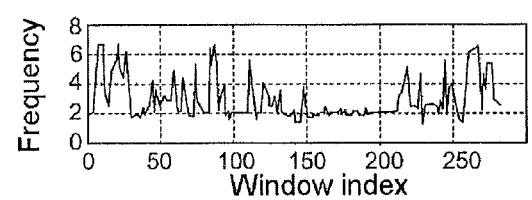

FIGS. 6a and 6b illustrate a first example. FIG. 6a illustrates a recording with a system according to one aspect of the invention worn on the belt. The detection is activated irrespective of the power of the measured signal along the mediolateral axis ML. FIG. 6a represents dominant frequencies $f_{ML}$ and $f_{AP}$ as a function of the window indices. They are dominant frequencies determined, for each time window, respectively along the mediolateral axis ML and the anteroposterior axis AP.

FIG. 6b representing the ratio for each time window between the dominant frequencies $f_{AP}$ and $f_{ML}$. In this example, the person is walking only between the time windows 160 and 210.

The ratio corresponding to these time windows is situated around the value 2. This test therefore makes it possible to determine a threshold, substantially equal to 2, in this instance, for example 1.9, above which the person is considered to be walking. This threshold may be determined manually, according to this type of test, or by known statistical analysis techniques making it possible to estimate the risks of false positives and false negatives.

It is now illustrated that the threshold is substantially equal to 2, that is to say close to 2, but not strictly equal to 2, an adjustment being able to be made during experimental tests. This adjustment may be manual or generated automatically, for example by determining a statistical distribution of the ratio between $f_{AP}$ and $f_{ML}$ and by estimating certain parameters of this distribution, for example the mean and the standard variation in the case in which the distribution is assumed to be normal.

Figure 7A:
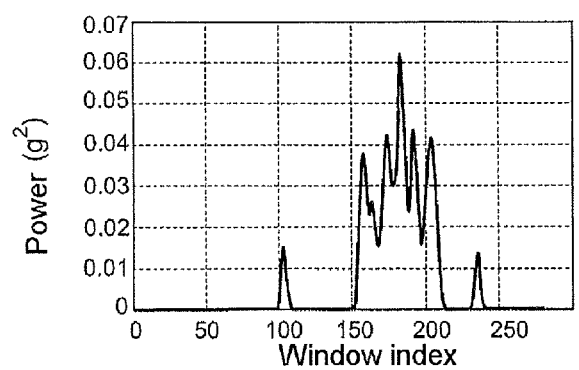
FIGS. 7a, 7b and 7c illustrate a second embodiment of the system according to one aspect of the invention.
Figure 7B:
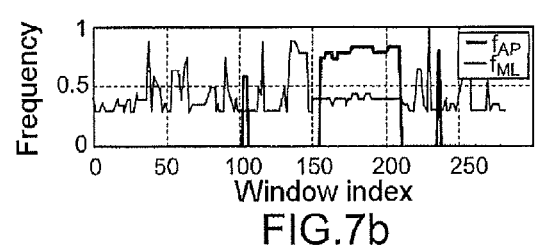
Figure 7C:
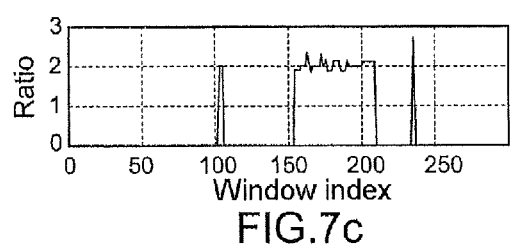

FIGS. 7a, 7b and 7c illustrate a second example in which the walking detection system is carried on a belt. A power threshold of the measured signal is imposed, for example on the signal measured along the mediolateral axis ML. Here, the power threshold below which it is not sought to detect a ratio $f_{AP}/f_{ML}$ is set at 0.01 g² (g=9.81 m·s⁻²). This power is represented in FIG. 7a of the power as a function of the window index. The power unit is in this instance the gravity constant squared. This curve therefore represents the power of the dominant frequency determined, along the mediolateral axis ML, for each time window.

FIG. 7b contains only the dominant frequencies $f_{AP}$ along the anteroposterior axis AP only for time windows having a signal measured along the mediolateral axis ML, the power of which is higher than the threshold mentioned. In this example, the user is walking between the time windows 155 and 210, and between the time windows 102 and 107.

In FIG. 7c, for each window corresponding to a walk of the user, a ratio is obtained that is substantially equal to 2, that is to say between 1.8 and 2.2. In this instance, the threshold could be set at 1.8 or 1.9. The power criterion is applied either to the signal measured along the mediolateral axis ML, or to the signal measured along the anteroposterior axis AP, or to both these signals, the thresholds then being able to be different.

Figure 8A:
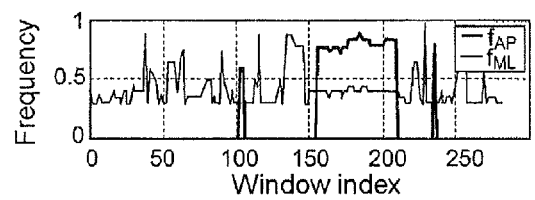
FIGS. 8a and 8b illustrate a third embodiment of the system according to one aspect of the invention.
Figure 8B:
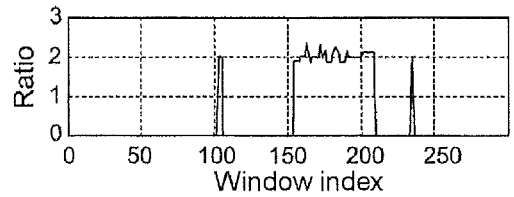
Figure 9A:
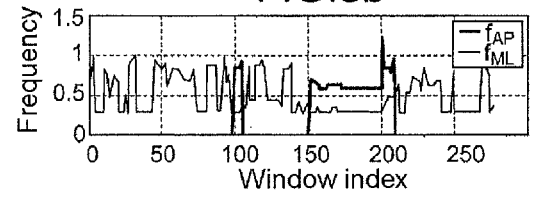
FIGS. 9a and 9b illustrate a fourth embodiment of the system according to one aspect of the invention.
Figure 9B:
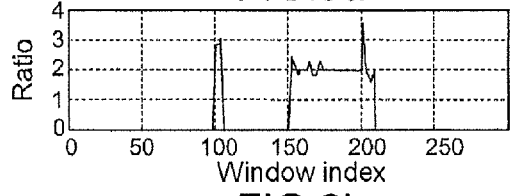
Figure 10A:
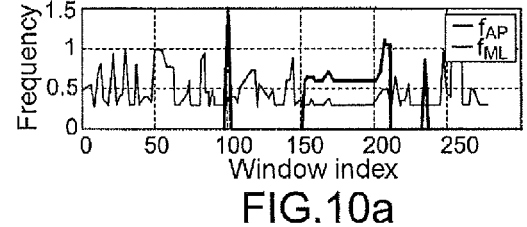
FIGS. 10a and 10b illustrate a fifth embodiment of the system according to one aspect of the invention.
Figure 10B:
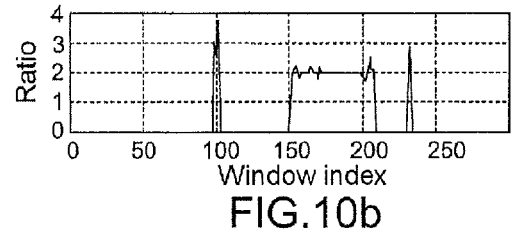

FIGS. 8a and 8b illustrate a third example for which FIG. 8b represents the ratio of the dominant frequency of a Euclidian norm of the vector of measurements transmitted by said sensor CM and the dominant frequency $f_{ML}$ of the signal of the second measurement axis.

Two other exemplary embodiments are illustrated respectively in FIGS. 9a, 9b and 10a, 10b, with a system attached respectively to the belt and to the torso.

These examples show that the user is walking between the time windows 150 and 200. It is particularly clearly illustrated in these two examples that wherever the system is placed on the upper portion of the body, the system is extremely reliable.

Embodiments of the present invention make it possible, at low cost, to detect with great precision a walking activity of a person.

Although the various embodiments of the present invention have described the detection of a walking phase in particular, it can be applied to a running phase, the frequency ranges for searching for a dominant frequency then being adjusted.

Moreover, embodiments of the present invention work without it being necessary to physically calibrate the movement sensor.

The invention claimed is:

1. A system for detecting the walk of a person, the system including a housing comprising at least a biaxial movement sensor, said housing configured to attach to an upper portion of the body of said person, so that a first measurement axis of said sensor provides measurements representative of an anteroposterior axis or a vertical axis of said body and so that a second measurement axis of said sensor provides measurements representative of a mediolateral axis of said body, said system further comprising a processor configured to analyze the measurements delivered by said sensor by performing steps comprising:
   processing over a time window the measurement signals delivered by said sensor to search for a dominant frequency in said signals, and
   detecting walking of the person as occurring when a ratio between the dominant frequency of the signal of the first measurement axis and the dominant frequency of the second measurement axis, or between the dominant frequency of a norm of the vector of measurements transmitted by said sensor and the dominant frequency of the signal of the second measurement axis, is substantially equal to two.

2. The system as claimed in claim 1, wherein said time window is a sliding window.

3. The system as claimed in claim 2, wherein the sliding window is five seconds long, with a partial overlap of four seconds between two consecutive windows offset by one second.

4. The system as claimed in claim 1, wherein said movement sensor is triaxial, the first measurement axis of said sensor coincides with the anteroposterior axis of said body, the second measurement axis of said sensor coincides with the mediolateral axis of said body, and the third measurement axis of said sensor coincides with the vertical axis of said body, and detecting the walk of the person further comprises detecting a ratio substantially equal to two between the dominant frequency of the signal of the first measurement axis and the dominant frequency of the second measurement axis, or between the dominant frequency of the signal of the third measurement axis and the dominant frequency of the second measurement axis, or between the dominant frequency of a norm of the vector of measurements transmitted by said sensor and the dominant frequency of the signal of the second measurement axis.

5. The system as claimed in claim 1, further comprising high-pass filters.

6. The system as claimed in claim 1, further comprising band-pass filters.

7. The system as claimed in claim 1, wherein said processor is internal or external to said housing, and wherein said movement sensor comprises wired or wireless transmitter for transmitting measurements to said processor.

8. The system as claimed in claim 1, wherein said movement sensor is a biaxial or triaxial accelerometer, or a biaxial or triaxial magnetometer or a biaxial or triaxial gyrometer.

9. The system as claimed in claim 1, wherein searching for the dominant frequency for the signals transmitted by the movement sensor comprises carrying out the search for the dominant frequency by a spectral analysis.

10. The system as claimed in claim 1, wherein searching for the dominant frequency is limited to a dominant frequency along the second axis $f_{ML}$ at frequencies of between 0.25 Hz and 1 Hz.

11. The system as claimed in claim 1, wherein searching for the dominant frequency is limited to a dominant frequency along the first axis, when the latter coincides with the anteroposterior axis, at frequencies between the dominant frequency along the second axis $f_{ML}$ increased by 0.2 Hz to 3 Hz.

12. The system as claimed in claim 1, wherein searching for the dominant frequency is limited to a dominant frequency along the first axis, when the latter coincides with the vertical axis, at frequencies between the dominant frequency along the second axis $f_{ML}$ increased by 0.2 Hz to 3 Hz.

13. The system as claimed in claim 1, wherein searching for the dominant frequency is limited to a dominant frequency, or for a norm of a vector of measurements transmitted by said movement sensor, at frequencies between the dominant frequency along the second axis $f_{ML}$ increased by 0.2 Hz to 3 Hz.

14. The system as claimed in claim 1, wherein detecting the walk of the person comprises detecting a ratio of said frequencies substantially equal to two, to within a variance, when the powers of the respective signals are also higher than a threshold.

15. The system as claimed in claim 1, wherein said housing is configured for attachment to the torso or to the sacrum of said person.

16. A method for detecting a walk of a person, the method comprising:

obtaining measurements from a biaxial or triaxial movement sensor, of movements along a first measurement axis of said sensor that is configured to provide measurements representative of an anteroposterior axis (AP) or a vertical axis of the body of said person and along a second measurement axis of said sensor that is configured to provide measurements representative of a mediolateral axis of said body, processing, over a time window, the measurement signals delivered by said movement sensor, said processing comprising a search for a dominant frequency in said signals, and detecting walking of said person as occurring when a ratio between the dominant frequency of the signal of the first measurement axis and the dominant frequency of the second measurement axis, or between the dominant frequency of a norm of the vector of measurements transmitted by said sensor and the dominant frequency of the signal of the second measurement axis, is substantially equal to two.

* * * * *